Figure 1:
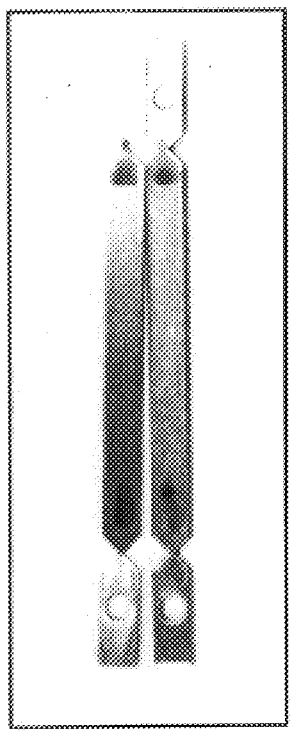

United States Patent

Smitkowski et al.

[11] Patent Number: 5,810,944
[45] Date of Patent: Sep. 22, 1998

[54] CLEANSER FOR SURGICAL INSTRUMENTS

[75] Inventors: Petra Smitkowski; Olaf Schreiber; Jürgen Staffeldt, all of Hamburg, Germany

[73] Assignee: Chemische Fabrik Dr. Weigert (GmbH & Co.), Hamburg, Germany

[21] Appl. No.: 737,017
[22] PCT Filed: Feb. 26, 1996
[86] PCT No.: PCT/EP96/00777
  § 371 Date: Oct. 29, 1996
  § 102(e) Date: Oct. 29, 1996
[87] PCT Pub. No.: WO96/26998
  PCT Pub. Date: Sep. 6, 1996
[51] Int. Cl.$^6$ .............. C11D 1/12; C11D 3/386; C11D 3/02; B08B 3/00
[52] U.S. Cl. .............. 134/42; 510/160; 510/161; 510/162; 510/218; 510/392; 510/393; 510/428; 510/501
[58] Field of Search .............. 510/160, 161, 510/162, 218, 392, 393, 428, 501; 134/42

[56] References Cited

U.S. PATENT DOCUMENTS

| H1513 | 1/1996 | Murch et al. .............. 252/546 |
| 4,456,544 | 6/1984 | Lupova et al. .............. 252/174.12 |
| 4,784,790 | 11/1988 | Disch et al. .............. 252/174.12 |
| 4,994,200 | 2/1991 | Disch et al. .............. 252/106 |
| 5,124,066 | 6/1992 | Russell .............. 252/174.12 |
| 5,234,832 | 8/1993 | Disch et al. .............. 435/264 |
| 5,489,531 | 2/1996 | Benson .............. 435/264 |
| 5,529,788 | 6/1996 | De Senna .............. 424/466 |
| 5,567,385 | 10/1996 | Miller et al. .............. 422/28 |
| 5,589,507 | 12/1996 | Hall, II et al. .............. 514/557 |

FOREIGN PATENT DOCUMENTS

| 0141607 | 5/1985 | European Pat. Off. . |
| 0199404 | 10/1986 | European Pat. Off. . |
| 0481663 | 4/1992 | European Pat. Off. . |
| 60-33090 | 2/1994 | Japan . |
| 60-33098 | 2/1994 | Japan . |

*Primary Examiner*—Kery Fries
*Attorney, Agent, or Firm*—Medlen & Carroll, LLP

[57] ABSTRACT

The invention relates to a cleanser concentrate having the following composition: 0.5–8.0% by weight of at least one $C_5$–$C_{12}$-alkyl sulphate salt, 4.0–15.0% by weight of at least one formulation aid, 4.0–10% by weight of at least one alkanolamine, and at least one commercially conventional proteolytic enzyme in an amount of 0.005–0.1 Anson and, if appropriate, conventional acids or bases for pH adjustment, conventional complexing agents and conventional preservatives, remainder, to 100% by weight, water. A process for cleaning surgical instruments has the following steps: applying a 0.5–100% strength aqueous solution of a cleanser concentrate according to one of claims 1–6 which has a pH of 8–9, allowing the solution to act at a temperature of room temperature to 55° C. for a period of 2 s–20 min, rinsing, thermal disinfection, if appropriate.

15 Claims, 1 Drawing Sheet

CLEANSER FOR SURGICAL INSTRUMENTS

The invention relates to a cleanser concentrate, in particular for the mechanical cleaning of medical and/or surgical instruments and/or apparatuses and to a process for carrying out this cleaning.

Surgical instruments and other medical equipment are conventionally mechanically cleaned in the hospital using alkaline cleansers and then chemically or thermally disinfected. Frequently, adequate cleaning action cannot be achieved by alkaline agents of this type. This is the case, in particular, when blood-contaminated surgical instruments are deposited immediately after their use, for example, in an aldehyde-containing disinfectant solution and remain therein initially until they are cleared out into the dishwasher for cleaning. The blood is coagulated by the disinfectants and the protein constituents contained in the blood are denatured by the aldehyde active disinfectant compound. Particularly persistent blood residues of this type can be removed in the prior art only by alkaline-active-chlorine-containing cleansers. The oxidizing active chlorine component effects the decomposition of the denatured protein constituents.

The disadvantages of the alkaline-active-chlorine-containing cleansers are that they contain dangerous substances which must be declared, that special safety precautions are necessary during their handling to protect the operating personnel and that they constitute undesirable environmental pollution in the waste water.

Enzyme-containing cleansers are likewise known from prior public use. However, the cleaning action of such enzymatic agents of the prior art is insufficient, in particular, for the removal of coagulated and denatured blood residues.

The object underlying the invention is to provide a cleanser concentrate and a process for cleaning medical and/or surgical instruments and/or apparatuses, in which the said disadvantages do not occur, or occur to a reduced extent, and which nevertheless ensures sufficient cleaning action.

The invention achieves this object by the features of Independent claims 1 and 7.

The invention relates to a cleanser concentrate having the following composition:

0.5–8.0% by weight of at least one $C_5$–$C_{12}$-alkyl sulphate salt, 4.0–15.0% by weight of at least one formulation aid, 4.0–10% by weight of at least one alkanolamine, and at least one commercially conventional proteolytic enzyme in an amount of 0.005–0.1 Anson units per g of concentrate and, if appropriate, conventional acids or bases for pH adjustment, conventional complexing agent (preferably in an amount of up to 10% by weight) and conventional preservatives, remainder, to 100% by weight, water.

Surprisingly, it has been found that, using this only weakly alkaline cleanser, not only blood residues dried on in air can be satisfactorily removed, but also preheated blood residues or blood residues denatured by aldehyde active disinfectant compounds can be satisfactorily factorily removed, from surgical instruments by means of mechanical cleaning. The claimed specific combination of an ionic surfactant (the alkyl sulphate salt), the ethanolamine and the proteolytic enzyme is essential for the success of the invention.

Preferably, the cleanser concentrate contains 1 to 6% by weight, more preferably 2 to 5% by weight, of $C_5$–$C_{12}$-alkyl sulphate salt. Preferably, sodium, potassium or ammonium salts are used. The chain length of the alkyl sulphate salts used is advantageously in the range $C_5$–$C_{10}$. Particular preference is given to isooctyl sulphates, amyl sulphates and mixtures thereof.

Suitable formulation aids (solubilizers) are, for example, sodium cumenesulphonate, sodium toluenesulphonate, sodium xylenesulphonate, urea, glycols, in particular polypropylene glycols and polyethylene glycols, methyl acetamide and fatty alcohols, such as cetyl alcohol. A preferred formulation aid is sodium cumenesulphonate. Advantageously, the formulation aids are present in the cleanser concentrate in an amount of 6 to 10% by weight.

The alkanolamine (preferably mono-, di- and/or triethanolamine) is advantageously used in an amount of 6 to 9% by weight. A particularly preferred alkanolamine is triethanolamine.

Proteolytic enzymes which are suitable are, in particular, commercially conventional proteases produced from bacterial strains.

The complexing agents which are added, if appropriate, can be homo-, co- or terpolymers based on acrylic acid or alkali metal salts thereof, in addition phosphonic acids or alkali metal salts thereof, such as 1-hydroxyethane-1,1-diphosphonic acid, aminotrismethylenephosphonic acid, ethylenediaminotetrakismethylenephosphonic acid, phosphonobutanetricarboxylic acid; tartaric acid, citric acid and gluconic acid; in addition nitrilotriacetic acid or ethylenediaminotetraacetic acid or salts thereof.

Preservatives which are suitable are, for example, p-hydroxybenzoic acid or its methyl ester, 5-bromo- 5-nitro-1,3-dioxane, salicylic acid, 2-naphthyl m,N-dimethylthiocarbanilate, 5-chloro-5-methyl-4-isothiazolin-3-one, 2-methyl-4-isothiazolin-3-one and mixtures of the two last-mentioned compounds. A preferred preservative is p-hydroxybenzoic acid or its methyl ester. Use of these preservatives avoids microbial and fungal contamination of the enzyme-containing cleanser concentrate.

The invention further relates to a process for the, in particular, mechanical cleaning of medical and/or surgical instruments and/or apparatuses, which is characterized by the following steps:

a) applying a 0.5–100% strength aqueous solution of a cleanser concentrate according to one of claims 1–6 which has a pH of 7.5–10, preferably 8–9, b) allowing the solution to act at a temperature of room temperature to 55° C. for a period of 2 s–20 min, c) rinsing, d) thermal disinfection, if appropriate.

The aqueous solution of the cleanser concentrate is preferably applied by spraying, but it can also be applied, for example, by dipping or pouring. The concentrate can be sprayed on in a very high concentration, if appropriate undiluted, as a fine mist and can initially act at this high concentration or undiluted. Then, if appropriate, additional water can be applied to the instruments to be cleaned and the cleanser solution thus diluted is circulated and, for example, applied again by spraying onto the instruments to be cleaned.

The period of action defined in step b) can include, after the application of the cleanser solution, action in the static state, i.e. without continuous application or spraying or mechanical circulation or agitation of the cleanser solution. Thus, for example, in particular highly concentrated cleanser solution can initially be sprayed on and, after the spraying, it is then allowed to act. However, the period of action can also include sections in which the cleanser solution is continuously reapplied or resprayed onto the instruments and/or is continuously mechanically circulated or agitated in some other manner. A combination of these two methods of action is also advantageous, that is initially allowing, in particular, highly concentrated cleanser solution to act in the static state and subsequent dilution of the cleanser with water with continuous circulation and repeated spraying.

The aqueous solution of the cleanser concentrate is advantageously applied as a 0.5 to 20% strength, preferably as a 0.5 to 10% strength, more preferably as a 1 to 5% strength, aqueous solution. During the time of action, the solution of the concentrate can be further diluted by additional water, but a minimum concentration of 0.5% should not be undershot. It should be noted that all percentages are by weight.

The solution is allowed to act in step b) preferably at 35°–50° C., more preferably at 40°–50° C. Temperatures at which the solution acts of somewhat above 40° C. have proved to be particularly advantageous, since, on the one hand, good cleaning action is achieved, and, on the other hand, the instruments to be cleaned are treated gently.

Advantageously, the time of action in step b) is 10 s to 10 min, preferably 30 s to 5 min.

The thermal disinfection according to step d) is preferably achieved with demineralized water at 85°–95° C., preferably 93° C. This water can simultaneously be used for rinsing in accordance with step c), so that, in this manner, steps c) and d) are combined. The disinfection can also be performed in a different manner, for example by means of chemical disinfectants.

In the context of the invention, the order of steps c) and d) can also be changed. The thermal disinfection step can, if appropriate, be performed with cleansing solution heated to the appropriate temperature (approximately 93° C.) instead of with fresh water.

If appropriate, when so-called discontinuous belt dishwashers are used, a number of cleaning steps can also be carried out sequentially with the cleanser concentrate of the invention. In this case, it is possible, for example, to use in one cleaning step an ultrasonic bath which is filled with an aqueous solution of the cleanser concentrate of the invention.

The invention achieves a good cleaning action, in particular even in barely accessible regions of surgical instruments, for example in the joint area of scissors. These areas especially may be cleaned only with difficulty using conventional cleansers.

The invention is described in more detail below on the basis of a preferred illustrative example.

A cleanser concentrate of the following composition was prepared:

Citric acid 1.6% by weight
NORAMER$^R$ [1]) 2000 (commercially conventional complexing agent based on carboxylate-sulphonate acrylic copolymers)
Sulfetal$^R$ [2]) 3.8% by weight
Sodium cumenesulphonate [3]) 8.0% by weight
p-Hydroxybenzoic acid 0.5% by weight
Triethanolamine 7.5% by weight
Esperase 8.0 L [4]) 2.0% by weight
Remainder (to 100% by weight) water

[1]) NorsoHaas S. A., Verneuil, En Halatte, France
[2]) Mixture of sodium isooctyl sulphate and sodium amyl sulphate, 38% strength, calculated on 100% strength concentration
[3]) 40% strength, calculated as 100% preparation
[4]) Novo Industries, Denmark The water used in this illustrative example is Hamburg municipal water.

Comparison tests on cleaning action

Stainless steel plates are furnished with a test fouling of 0.1 ml of fresh pig's blood per plate. The pig's blood is dried on for 40 min at room temperature. The test plates are then dipped for 1 min in a 0.1% strength solution of glutardialdehyde and dried at room temperature for a further 60 min. The glutardialdehyde solution denatures the blood protein and thus establishes the conditions which are also present in the case of used surgical instruments kept in disinfectants.

Four aqueous cleansing solutions are prepared:
1. a 10% strength solution of the concentrate of the invention according to the illustrative example
2. a 10% strength solution of a commercially conventional alkaline cleanser of the following composition:
   46% pentapotassium triphosphate (50% strength)
   24% potassium hydroxide solution (45% strength)
   30% sodium waterglass (38° dBe')
3. a 10% strength solution of a commercially conventional alkaline intensive cleanser of the composition:
   40% nitrilotriacetic acid, sodium salt (40% strength)
   32% sodium hydroxide solution (45% strength)
   4% amphoteric surfactant (40% strength)
   Remainder (to 100%) water
4. a 10% strength solution of a commercially conventional alkaline active-chlorine-containing cleanser having the composition:
   16% potassium hydroxide solution (45% strength)
   28% pentapotassium triphosphate (50% strength)
   16% waterglass (38° Be')
   5% pentasodium triphosphate
   21% chlorine bleach solution (150–160 g of active chlorine/l)
   Remainder (to 100%) water The solutions are heated to 40° C. and two fouled test plates are dipped each time into the static solution. The plates are taken out again after a time of action of 5 and 10 min, respectively.

Figure 2:
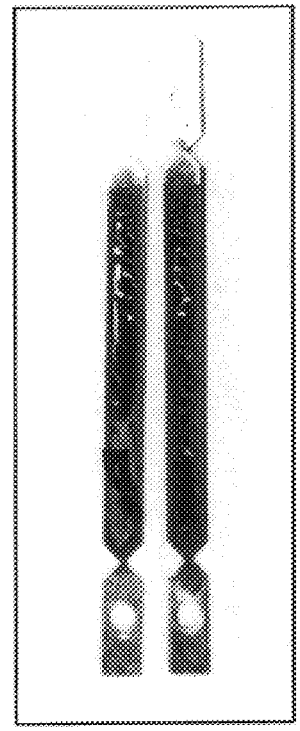
Figure 3:
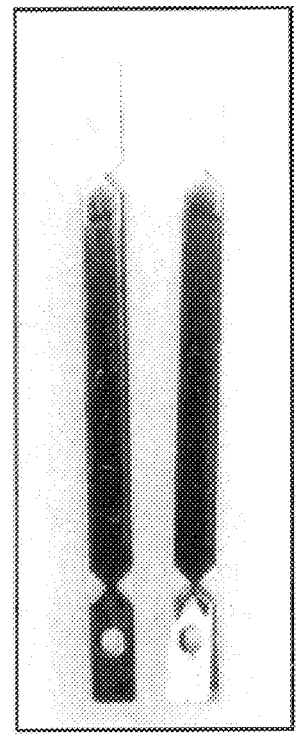
Figure 4:
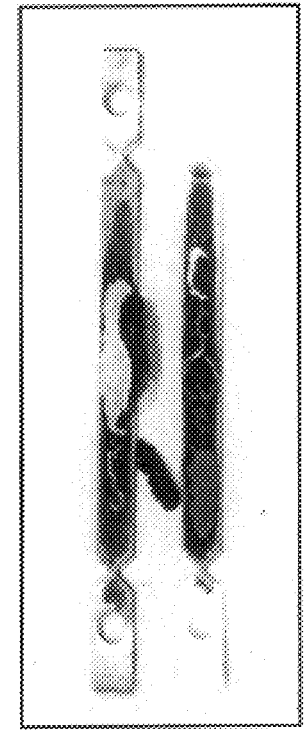

The cleaning action of the solutions 1 to 4 is shown in FIGS. 1 to 4. In each of the figures, the left test plate has a time of action of 5 min, and the right plate has a time of action of 10 min.

It is clearly seen that the alkaline cleansers display only poor cleaning action and crusts which are still thick are present, which at best flake off. After the treatment with the cleansing concentrate of the invention, only slight residual traces of denatured blood are present; the majority of the blood has been removed. When these comparison tests are evaluated, it should be taken into account that, in practice, in mechanical cleaning, because of the agitation and circulation of the cleanser solution, markedly better cleaning actions result.

Process Examples for Mechanical Cleaning

1. In a single-tank dishwasher, the instruments to be cleaned are first prerinsed with cold water. The dishwasher is then filled with cold water and the cleanser concentrate according to the illustrative example is added at a concentration of 1.5%. The cleanser solution is heated to 40°–45° C. and kept at this temperature for 5 min. The contents are then rinsed with water and, finally, thermally disinfected with demineralized water at 93° C. This water is simultaneously used for rinsing.

2. Cleaning using a discontinuous belt unit
In a discontinuous belt unit, the instruments to be cleaned are run successively into different cleaning chambers. In this illustrative example, a 3-chamber unit is used.

In the first chamber, precleaning is first performed with cold water for a period of 30 s, then follows cleaning with a 1% strength aqueous concentration of the cleanser concentrate according to the illustrative example for a period of 5 min at a temperature of 40° C. Subsequent to this, water is again used for rinsing for 30 s.

In the second chamber, the instruments are treated in an ultrasonic bath for 5.5 min at 35° C. with a 2% strength aqueous solution of the cleanser concentrate according to the illustrative example.

In the third chamber, rinsing and simultaneous thermal disinfection with demineralized water at 93° C. is performed for 6 minutes.

We claim:

1. An aqueous detergent for use in cleaning medical and surgical instruments solution, comprising:

0.5–8.0% by weight of a mixture of a first $C_5$–$C_{10}$ alkyl sulphate and a second $C_5$–$C_{10}$ alkyl sulphate, 4.0–15.0% by weight of at least one formulation aid, 4.0–10% by weight of at least one alkanolamine, and at least one proteolytic enzyme.

2. The solution of claim 1, wherein said first $C_5$–$C_{10}$-alkyl sulphate salt is sodium amyl sulphate.

3. The solution of claim 1, wherein said second $C_5$–$C_{10}$-alkyl sulphate salt is sodium isooctyl sulphate.

4. The solution of claim 1, wherein said solution is in contact with a medical instrument.

5. An aqueous solution, comprising:

0.5–8.0% by weight of a mixture of sodium amyl sulphate and sodium isooctyl sulphate, 4.0–15.0% by weight of a formulation aid selected from the group consisting of sodium cumenesulphonate, sodium toluenesulphonate, and sodium xylenesulphonate, 4.0–10% by weight of an alkanolamine selected from the group consisting of monoethanolamine, diethanolamine and triethanolamine, and at least one proteolytic enzyme.

6. The solution of claim 5, wherein said mixture is 2–5% by weight.

7. The solution of claim 6, wherein said mixture is 3.8% by weight.

8. A process, comprising:

a) providing:

i) an instrument to be cleaned, and ii) an aqueous solution, comprising 0.5–8.0% by weight of a mixture of a first $C_5$–$C_{10}$ alkyl sulphate and a second $C_5$–$C_{10}$ alkyl sulphate salt, 4.0–15.0% by weight of at least one formulation aid, 4.0–10% by weight of at least one alkanolamine, and at least one proteolytic enzyme; and b) applying said aqueous solution to said instrument.

9. The process of claim 8, wherein said instrument is a surgical instrument.

10. The process of claim 8, wherein said applying comprises spraying on said aqueous solution.

11. The process of claim 8, wherein, prior to said applying step, said aqueous solution is diluted.

12. The process of claim 11, wherein said aqueous solution is allowed to act at a temperature of between 35° and 50° C.

13. The process of claim 12, wherein said aqueous solution is allowed to act at a temperature of between 40° and 50° C.

14. The process of claim 8, wherein said first $C_5$–$C_{10}$-alkyl sulphate salt is sodium amyl sulphate.

15. The process of claim 8, wherein said second $C_5$–$C_{10}$-alkyl sulphate salt is sodium isooctyl sulphate.

* * * * *